(12) United States Patent
Sung et al.

(10) Patent No.: US 8,137,674 B2
(45) Date of Patent: Mar. 20, 2012

(54) COMPOSITIONS COMPRISING HPV POLYPEPTIDES AND IMMUNOENHANCEMENT PEPTIDES FOR THE TREATMENT AND PREVENTION OF CERVICAL CANCER

(75) Inventors: Young Chul Sung, Pohang-si (KR); Hyun Tak Jin, Pohang-si (KR); Sang Hwan Seo, Pohang-si (KR); Sang Hoon Park, Anyang-si (KR); Je-In Youn, Chungsheongbuk-do (KR)

(73) Assignees: Postech Foundation, Pohang-Si (KR); Genexine Co., Ltd., Seoul (KR)

( * ) Notice: Subject to any disclaimer, the term of this patent is extended or adjusted under 35 U.S.C. 154(b) by 158 days.

(21) Appl. No.: 12/297,407

(22) PCT Filed: Apr. 19, 2006

(86) PCT No.: PCT/KR2006/001448
§ 371 (c)(1),
(2), (4) Date: Mar. 12, 2009

(87) PCT Pub. No.: WO2007/119896
PCT Pub. Date: Oct. 25, 2007

(65) Prior Publication Data
US 2009/0305979 A1  Dec. 10, 2009

(51) Int. Cl.
*A61K 39/00* (2006.01)
(52) U.S. Cl. .................. 424/192.1; 530/300; 424/204.1
(58) Field of Classification Search .................. None
See application file for complete search history.

(56) References Cited

U.S. PATENT DOCUMENTS

2004/0110925 A1   6/2004   Hu et al.
2007/0014810 A1*  1/2007   Baker et al. ................ 424/186.1

OTHER PUBLICATIONS

Hung et al, Cancer Research, 2001, vol. 61, pp. 1080-1088.*
International Search Report prepared by the Korean Intellectual Property Office on Jan. 12, 2007 for International Application No. PCT/KR2006/001448; Applicants, Postech Foundation and Genexine Co., Ltd.
Lasaro, M.O. et al. "Anti-tumor DNA vaccines based on the expression of human papillomavirus-16 E6/E7 oncoproteins genetically fused with the glycoprotein D from herpes simplex virus-1" Microbes Infect., Dec. 2005, vol. 7, No. 15, pp. 1541-1550.
Hill, S.C. at al. "Activation of CD40 in cervical carcinoma cells facilitates CTL responses and augments chemotherapy-induced apoptosis" J Immunol., Jan. 2005, vol. 174, No. 1, pp. 41-50.
Le Roux, L.G. et al. "Nuclear entry of high-risk human papillomavirus type 16 E6 oncoprotein occurs via several pathways" J Virol., Feb. 2003, vol. 77, No. 4, pp. 2330-2337.

* cited by examiner

*Primary Examiner* — Ali R. Salimi
(74) *Attorney, Agent, or Firm* — Bryan Cave LLP

(57) ABSTRACT

The present invention relates to a fusion protein comprising a fusion polypeptide of E6 and E7 of a human papilloma virus, a signal peptide for secreting the polypeptide out of the cell, and an immune enhancing peptide for a subject; a polynucleotide encoding the fusion protein; and a vector containing the polynucleotide. The present invention further relates to a pharmaceutical composition comprising the fusion protein or the vector; and a method for treating a disease caused by a human papilloma virus using the pharmaceutical composition.

4 Claims, 3 Drawing Sheets

[FIG. 1]
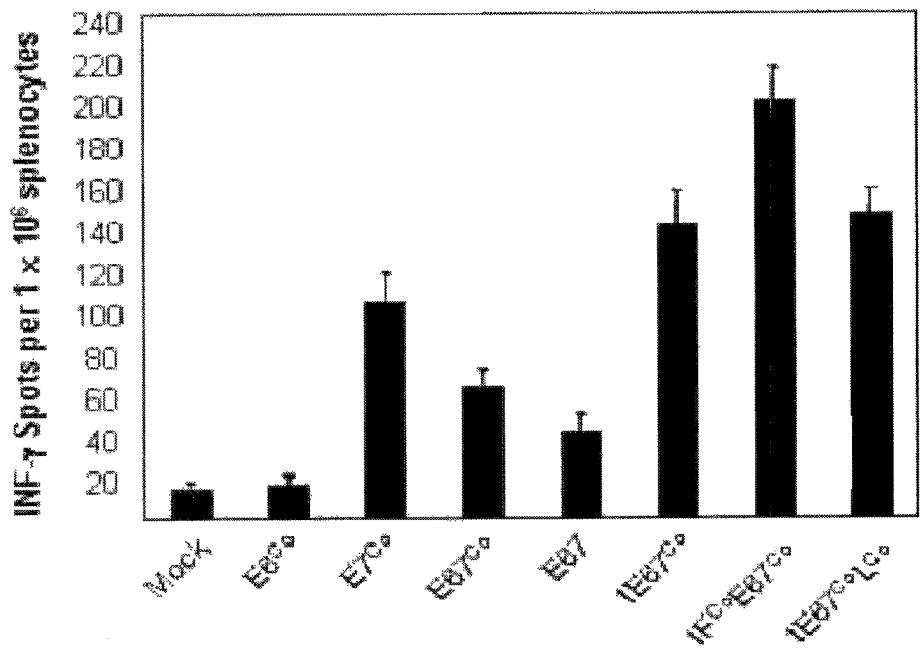
[FIG. 2]
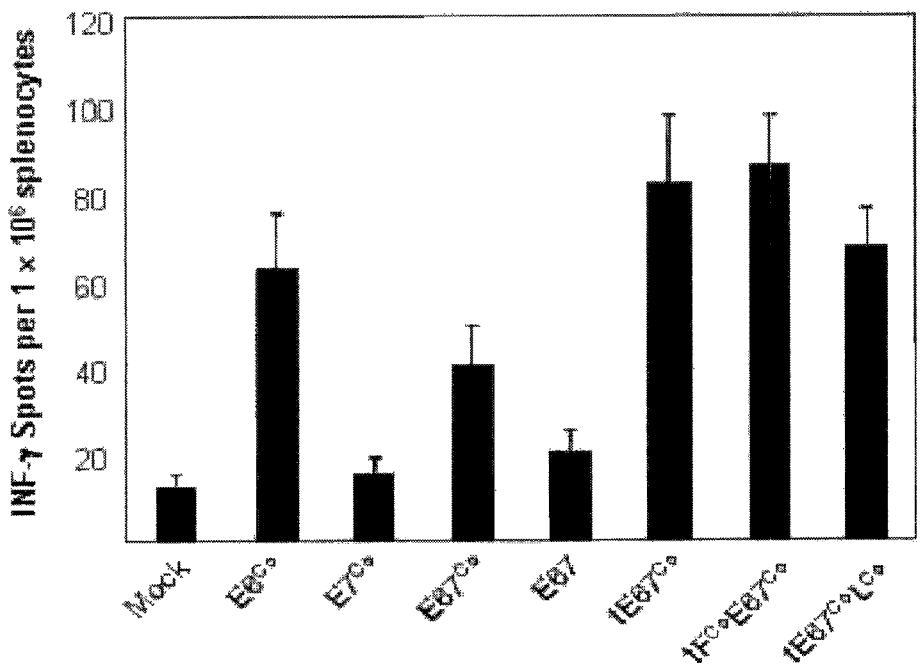

[FIG. 3]
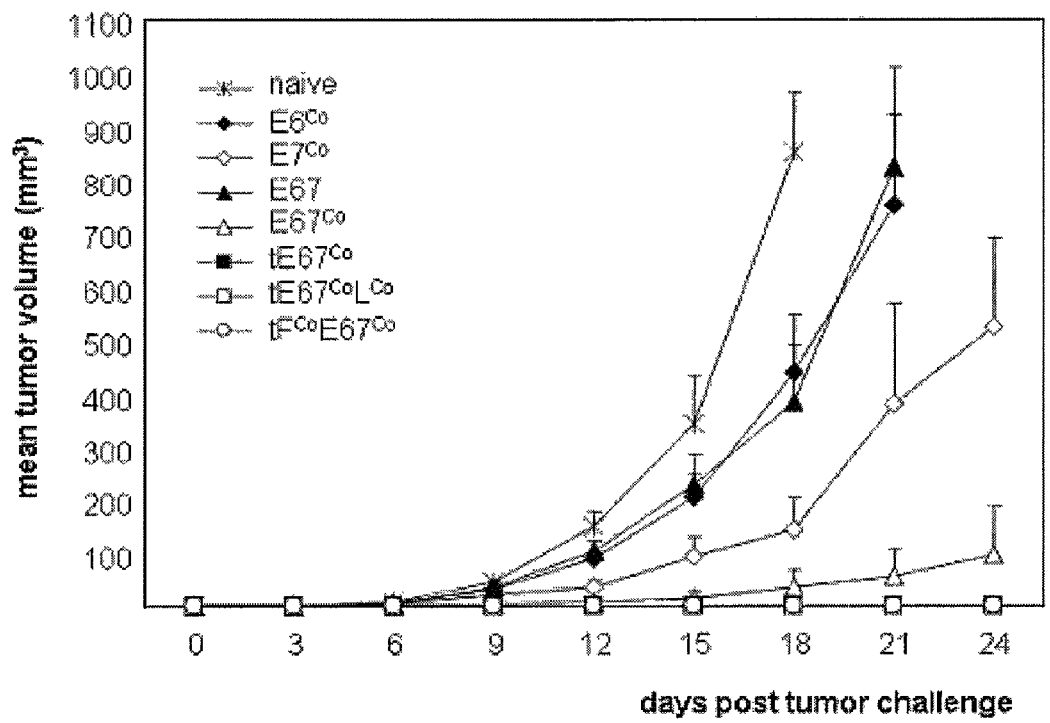
[FIG. 4]
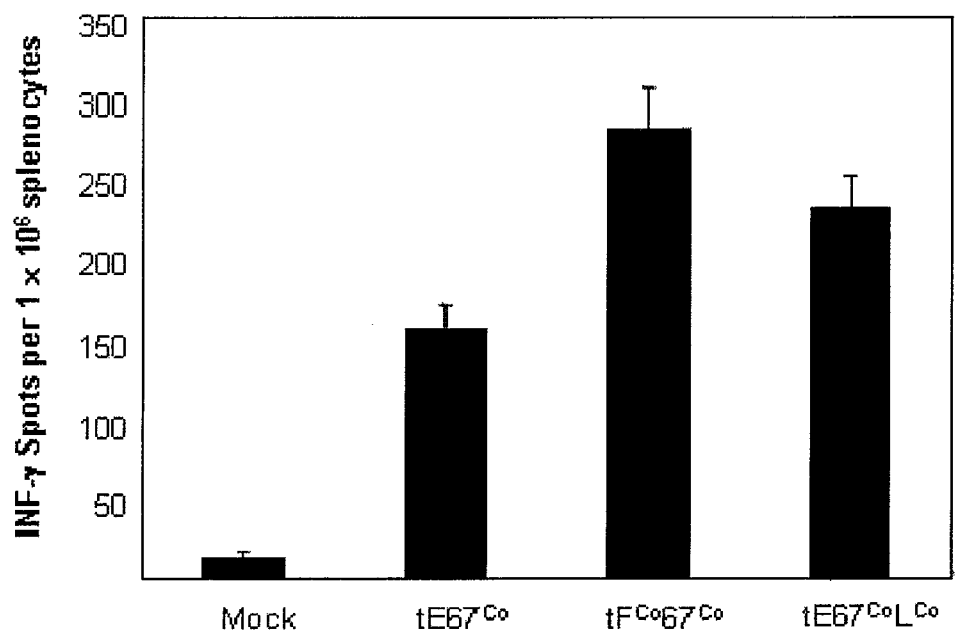

[FIG. 5]
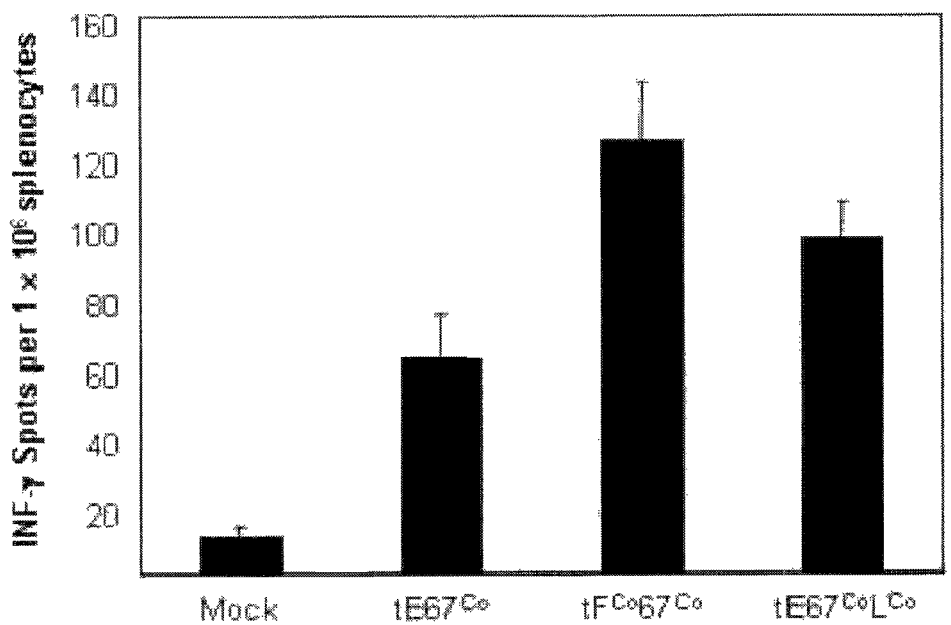
[FIG. 6]
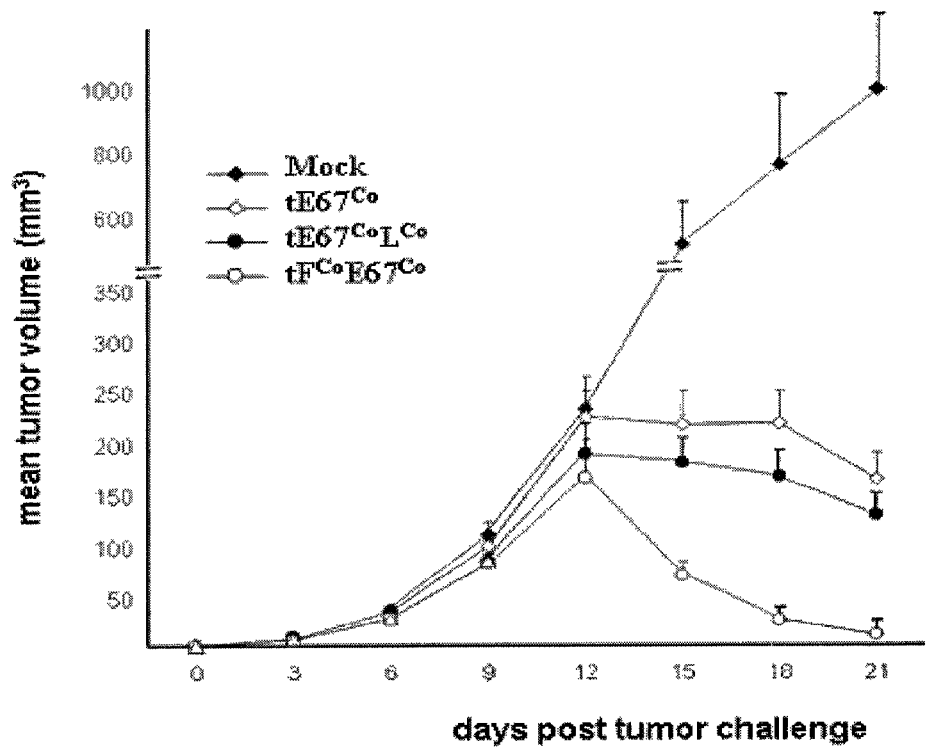

US 8,137,674 B2

COMPOSITIONS COMPRISING HPV POLYPEPTIDES AND IMMUNOENHANCEMENT PEPTIDES FOR THE TREATMENT AND PREVENTION OF CERVICAL CANCER

CROSS REFERENCE TO RELATED APPLICATIONS

This application is a national stage application under 35 U.S.C. 371 of PCT Application No. PCT/KR2006/001448 having an international filing date of Apr. 19, 2006, which designated the U.S., the entire disclosure of which is hereby incorporated herein by reference.

TECHNICAL FIELD

The present invention relates to a fusion protein comprising a fusion polypeptide of E6 and E7 of a human papilloma virus (HPV), a signal peptide for secreting the polypeptide out of the cell, and an immune enhancing peptide for a subject; a polynucleotide encoding the fusion protein; a vector containing the polynucleotide; a pharmaceutical composition comprising the fusion protein or the vector; and a method for treating a disease caused by a human papilloma virus using the pharmaceutical composition.

BACKGROUND ART

Cervical cancer has become the second leading cause of death of cancers, causing 250,000 deaths worldwide annually. Cervical cancer has been known to be mostly caused by a human papilloma virus (HPV) infection (zur Hausen, H et al. Biochem Biophys Acta 1996, 1288; F55-F78). Among hundreds of types of HPVs, HPV16 is known as the leading cause of cervical cancer (Mark H et al. J Natl Cancer Inst 1993, 85; 958-964). Among the HPV proteins, E6 and E7 proteins play critical roles in the occurrence of cervical cancer as oncogenes, and it has been reported that they are the major proteins which are expressed in about 99% of the tumors caused by HPVs. As a result, E6 and E7 proteins have become a major target antigen in the preparation of a vaccine to treat and prevent the cervical cancer (von Knebel Doeberitz et al. Int. J. Cancer 1992, 51; 831-834). E6 prevents apoptosis of the cells by inducing decomposition of a tumor-inhibiting protein p53, and E7 binds to a retinoblastoma protein (Rb) which is a cellular tumor suppressor, to inactivate the protein, and then to induce the cells to enter an S phase in the cell cycle (Cobrinik et al., Trends Biochem Sci 1992, 17:312-5).

A clinical test using a composition expressing a nucleic acid base sequence which expresses HPV16 E6 and E7 proteins at the same time was performed in order to treat the cervical cancer, but its therapeutic effect was not significant (Garcia F et al. Obstet Gynecol 2004, 103; 317-326). Further, International Patent Publication WO 2004/030636 discloses a fusion polypeptide comprising E6 and E7, wherein the E6 is at an amino terminal or a carboxyl terminal, and a polynucleotide encoding the fusion polypeptide. However, the polypeptide as disclosed in this document still has limitation in treating the cervical cancer caused by HPV.

Therefore, the present inventors have found that a fusion protein comprising an E6/E7 fusion polypeptide of HPV bonded with a secretory peptide and an immune enhancing peptide improves immune responses, and is effective in treatment and prevention of the tumors caused by HPV, thereby completing the present invention.

DISCLOSURE

Technical Solution

It is an object of the present invention to provide a fusion protein which is highly effective in the treatment and prevention of diseases caused by HPV.

It is another object of the present invention to provide a polynucleotide encoding the fusion protein.

It is a still another object of the present invention to provide a recombinant vector comprising the polynucleotide.

It is a still another object of the present invention to provide a pharmaceutical composition comprising the fusion protein and the recombinant vector.

It is a still another object of the present invention to provide a method for the treatment or prevention of diseases caused by HPV using the pharmaceutical composition in a subject.

DESCRIPTION OF DRAWINGS

FIG. 1 is a graph illustrating the comparison results of the E7 specific CD8+ T cell responses produced by vaccination of plasmid DNAs which express Mock, $E6^{Co}$, $E7^{Co}$, E67 and $E67^{Co}$, $tE67^{Co}$, $tF^{Co}E67^{Co}$ and $tE67^{Co}L^{Co}$ in a C57BL/6 mouse model.

FIG. 2 is a graph illustrating the comparison results of the E6 specific CD8+ T cell responses produced by vaccination of Mock, $E6^{Co}$, $E7^{Co}$, E67 and $E67^{Co}$, $tE67^{Co}$, $tF^{Co}E67^{Co}$ and $tE67^{Co}L^{Co}$ in a C57BL/6 mouse model.

FIG. 3 is a graph illustrating the comparison results of the prophylactic antitumor effects against subcutaneous injection of TC-1 tumor cells, indicated by the increase in the volume of tumor mass, in vaccinated C57BL/6 mice with Mock, $E6^{Co}$, $E7^{Co}$, E67 and $E67^{Co}$, $tE67^{Co}$, $tF^{Co}E67^{Co}$ and $tE67^{Co}L^{Co}$.

FIG. 4 is a graph illustrating the comparison results of the E7 specific CD8+ T cell responses produced by treatment with mock, $tE67^{Co}$, $tF^{Co}E67^{Co}$ and $tE67^{Co}L^{Co}$ in a C57BL/6 mouse bearing TC-1 tumors.

FIG. 5 is a graph illustrating the comparison results of the E6 specific CD8+ T cell responses produced by treatment with mock, $tE67^{Co}$, $tF^{Co}E67^{Co}$ and $tE67^{Co}L^{Co}$ in a C57BL/6 mouse bearing TC-1 tumors.

FIG. 6 is a graph illustrating the comparison results of the therapeutic antitumor effects produced by treatment with mock, $tE67^{Co}$, $tF^{Co}E67^{Co}$ and $tE67^{Co}L^{Co}$ in a C57BL/6 mouse bearing TC-1 tumor as a therapeutic model.

BEST MODE

According to an aspect of the present invention, there is provided a fusion protein comprising a fusion polypeptide of E6 and E7 of a human papilloma virus (HPV), a signal peptide for secreting the polypeptide out of the cell, and an immune enhancing peptide for a subject.

The E6 and E7 that constitute the fusion polypeptide of the present invention are antigen proteins derived from human papilloma virus (HPV) types 16, 18, 31, 33, 45 and 51, and they are preferably E6 and E7 antigen proteins derived from human papilloma virus types 16 (HPV16) or 18 (HPV18).

In the present invention, the expression "fusion polypeptide of E6 and E7 of a human papilloma virus" refers to a fusion protein of a polypeptide in which each of E6 and E7 has a natural amino acid sequence, or either of E6 and E7 has an amino acid mutant of a natural amino acid sequence. As used herein, the term "mutant" refers to a polypeptide, which has a different amino acid sequence from a natural amino acid sequence by subjecting at least one amino acid residue to deletion, insertion, conservative substitution, or a combination thereof, but has substantially the same immunogenicity as that of a natural E6 and E7 polypeptide, and can occur naturally or artificially. In one embodiment, the mutants may be exemplified by SEQ ID NO: 4, in which the 63rd and 106the cysteins are substituted with glycines in the amino acid sequence encoding E6 polypeptide of a human papilloma virus type 16 (HPV16); SEQ ID NO: 6, in which the 24th cysteine and the 26th glutamic acid are substituted with glycines in the amino acid sequence encoding E7 polypeptide of HPV16; SEQ ID NO: 10, in which the 65th and 108th cysteine are substituted with glycines in the amino acid sequence encoding E6 polypeptide of HPV18; or SEQ ID NO: 12, in which the 27th cysteine and the 29th glutamic acid are substituted with glycines in the amino acid sequence encoding E7 polypeptide of HPV18.

The fusion polypeptide of E6 and E7 of a human papilloma virus of the present invention may be in the form of an E6/E7 fusion polypeptide, in which E6 is at the amino terminal with respect to E7, that is, E6 is followed by E7 (E6/E7 fusion polypeptide); or in which E6 is at the carboxyl terminal with respect to E7, that is, E7 is followed by E6 (E7/E6 fusion polypeptide). In specific embodiments, the fusion polypeptide may be exemplified by the HPV16 E6/E7 fusion polypeptide of SEQ ID NO: 8, or the HPV18 E6/E7 fusion polypeptide of SEQ ID NO: 14.

In the present invention, the phase "signal peptide" refers to a peptide consisting of about 20 to 30 amino acids, which secrets a protein expressed within a cell, in particular, a protein comprising an E6/E7 fusion polypeptide, out of the cell. The signal peptide for secreting the polypeptide out of the cell, and a nucleic acid sequence encoding the same are referred to as a "secretory signal sequence". The E6 and E7 antigens of the present invention is a protein expressed within the nucleus of the cell which has been infected with a virus (a nucleus protein), and as a result, has weak immunity. Thus, the signal peptide expressed by the secretory signal sequence can induce the secretion of E6 and E7 antigens out of the cell to increase an antigen-specific humoral immune response, and a cellular immune response. Therefore, for the signal peptide of the present invention, secretory signal sequences, etc. of tPA, HSV gDs, and growth hormone can be used, but are not limited thereto. Preferably, a signal peptide used in higher eukaryotic cells including a mammal, more preferably tPA (tissue plasminogen activator) can be used.

As used herein, the phrase "immune enhancing peptide" refers to a peptide which activates cells associated with immune responses to increases the immune responses (e.g., dendritic cells, etc.). Examples of the immune enhancing peptides include a CD40 ligand, an Flt3 ligand, a Flagellin, and OX40. In the present invention, at least one immune enhancing peptide can be selected from the above-listed peptides to use, and preferably the peptide can be selected individually to use. In specific embodiments of the present invention, the CD40 ligand and the Flt3 ligand are used individually or in a combination thereof. The "Flt3 ligand" of the present invention is a factor which induces the proliferation and maturation of the dendritic cells (DC), which increase an immune response by an antigen, and is highly effective in reducing a tumor when fused with the tumor antigen. As used herein, the phrase "CD40 ligand" is a ligand which interacts with CD40 present on the surfaces of antigen presenting cells (APC) such as dendritic cells to activate the dendritic cells, etc.

As used herein, the "subject" encompasses mammals such as a human, a monkey, a mouse, a pig, a cow, and a rabbit, but is not limited thereto.

The fusion protein of the present invention is highly effective in antigen-specific immune responses, and in inhibition of occurrence and growth of a tumor. Indeed, a fusion polypeptide of E6 and E7 of a human papilloma virus induced both E6- and E7-specific CD8$^+$ T cell responses and showed stronger antitumor effect than did E6 or E7. In addition, it was found that a fusion protein, in which the fusion polypeptide of E6 and E7 of a human papilloma virus is bound with a signal peptide and an immune enhancing peptide, results in a highly effective antigen-specific immune response, and inhibits the occurrence and growth of a tumor. In specific embodiments, it was found that a fusion protein, in which the fusion polypeptide of E6 and E7 of a human papilloma virus is bound with tPa as a signal peptide, and a Flt3 ligand and/or a CD40 ligand as an immune enhancer is highly effective in an antigen-specific immune response, inhibition of occurrence and growth of a tumor, and inhibition of a tumor size, as compared with each of E6 and E7 of a human papilloma virus. Accordingly, the fusion protein of the present invention can be used for the treatment and prevention of a tumor.

Another embodiment of the present invention relates to a polynucleotide encoding the fusion protein.

The polynucleotide of the present invention can be prepared by a chemical synthesis method, or a genetic engineering technology. The chemical synthesis methods are known to a skilled person in the art, and any of the methods can be used. Further, it may be purchased from a commercial synthesizer or manufacturer. In the case where it is prepared by a genetic engineering technology, for example, nucleic acid fragments encoding commercially known fusion polypeptide of E6 and E7, signal peptide, and immune enhancing peptide, respectively, and linking the fragments to fit with the frames. A method for obtaining the nucleic acid fragments is known in the art, and a skilled person in the art can link them with an appropriate restriction enzyme. In specific embodiments of the present invention, a method for preparing a polynucleotide by chemical synthesis is disclosed.

Still another embodiment of the present invention relates to a recombinant vector comprising the polynucleotide.

As used herein, the term "vector" refers to a genetic construct comprising a foreign DNA, which had been inserted into a genome encoding a polypeptide. As used herein, the phrase "expression vector" refers to a vector, in which a nucleic acid sequence encoding a secretory signal sequence, a nucleic acid sequence encoding a fusion polypeptide of E6 and E7 of a human papilloma virus, and a nucleic acid sequence encoding an immune enhancing peptide, or the like, are inserted into a genome, and examples thereof include a plasmid vector, a cosmid vector, a bacteriophage, a yeast vector, and a virus vector, such as an adenovirus vector, a retrovirus vector, an adeno-associated virus vector.

As used herein, the phrase "secretory signal sequence" refers to a nucleic acid sequence encoding a peptide which secretes a tumor antigen expressed within a cell out of the cell and allows it to be recognized by immune cells, and examples thereof include such secretory signal sequences as tPA, HSV gDs, and a growth hormone. Preferably, a secretory signal sequence used in higher eukaryotic cells of a mammal, more preferably tPA (tissue plasminogen activator) can be used. Further, the secretory signal sequence of the present invention can be used after substituting with a codon having a high expression frequency in a host cell.

As used herein, the expression "nucleic acid sequence encoding the immune enhancing peptide" refers to a nucleic acid sequence encoding a peptide which increases an immune response by the activation of cells associated with immune responses (e.g., dendritic cells, etc.). Examples of the immune enhancing peptides include a CD40 ligand, an Flt3 ligand, a Flagellin, and OX40. In the present invention, at least one can be selected from these immune enhancing peptides to use, and preferably each of the peptides can be selected to use. In specific embodiments of the present invention, the CD40 ligand and the Flt3 ligand are used individually or in a combination thereof. The nucleic acid sequence encoding the immune enhancing peptide can be used after substituting with a codon having a high expression frequency in a host cell.

The polynucleotide contained in recombinant vector of the present invention can be substituted with a codon having a high expression frequency in a host cell. As used herein, the expression "substitution with a codon having a high expression frequency in a host cell", or "codon optimization" refers to substituting a codon having high preference in some hosts among the codons designating the amino acids upon transcription and translation of DNAs to a protein in a host cell, with a codon having a higher preference, and thus increasing the expression efficiency of the amino acid or protein, encoded by the nucleic acids. Herein, the term "host cell" encompasses a prokaryotic cell, or a eukaryotic cell, and the eukaryotic cells includes a lower eukaryotic cell such as a fungus and a yeast, as well as a higher eukaryotic cell such as a mammal.

The polynucleotide encoding the fusion polypeptide of E6 and E7 of a human papilloma virus, which is contained in the recombinant vector of the present invention, can be substituted with some of the nucleic acid sequences encoding E6 and E7 so as to avoid the generation of oncogenicity, in addition to the codon optimization.

For the fusion polypeptide of E6 and E7 of a human papilloma virus of the present invention, the expression of E6 and E7 into a fusion polypeptide to be used as an immunogen more effectively induces an antitumor effect, as compared with individual expression of E6 and E7 to be used as an immunogen. Further, the nucleic acid sequence encoding the fusion polypeptide of E6 and E7 substituted with a codon having a high expression frequency in a host cell more effectively induces an antigen-specific immune response, as compared with that unsubstituted. Further, even if there occurs a mutation such that some nucleic acid sequence of E6 and E7 is deleted to avoid oncogenicity, an immune response can be effectively induced. In specific embodiments, the nucleic acid sequences of the E6/E7 fusion polypeptide having fusion with the polypeptides of the codon-optimized and -mutated HPV16 E6 and E7, or HPV18 E6 and E7 is depicted in SEQ ID NOs: 7 and 13. Further, the co-expression of the E6/E7 fusion polypeptide, and a signal peptide by a secretory signal sequence, and an immune enhancing peptide increases the effectiveness of an antigen-specific immune response, and inhibits the size and occurrence of a tumor, as compared with the expression of the E6/E7 fusion polypeptide alone.

The recombinant vector of the present invention can comprise a nucleic acid encoding the fusion protein in the form adapted for expression of the nucleic acids encoding the fusion protein of the present invention in the host cell. That is, the recombinant vector of the present invention comprises at least one regulatory sequence to be used for expression, selected on the basis of the host cells, and the regulatory sequence is operatively linked with a nucleic acid sequence to be expressed. The expression "operatively linked with" refers to a nucleotide sequence being linked to the regulator sequence so as to be expressed (for example, in an in-vitro transcription/translation system, or in a host cell). The phrase "regulatory sequence" is intended to include a promoter, an enhancer, and other regulatory elements (e.g., polyadenylation signal). The regulatory sequence encompasses one directing a desired nucleic acid to be expressed constitutively, and one directing a desired nucleic acid to be expressed in a specific host cell only (e.g., tissue-specific regulatory sequence) in a number of host cells. It will be understood by a skilled person in the art that the design of the expression vector can vary depending on the factors such as selection of the host cells to be transformed, and levels of expression of a desired protein. The expression vector of the present invention can be introduced into a host cell to express the fusion protein.

The vector of the present invention can be prepared, for example, by a standard recombination DNA technology, and the standard recombination DNA technologies include, for example, ligation of a blunt end and a sticky end, treatment with a restriction enzyme to provide an appropriate end, removal of a phosphate group by treatment with an alkaline phosphatase to avoid a non-specific binding, and enzymatic bonding by a T4 DNA ligase. Each of DNAs which encode signal peptides, fusion polypeptides of E6 and E7 of a human papilloma virus, and immune enhancing peptides, which are obtained by a chemical synthesis method, or a genetic engineering technology can be recombined with a vector containing an appropriate regulatory sequence to provide the vector of the present invention. The vector containing the regulatory sequence can be commercially available, or prepared, and in the present invention, it was prepared using pGX10, which is a vector used to prepare a vaccine as disclosed in Korean Patent Application Publication No. 2003-47667.

Still another embodiment of the present invention relates to a recombinant vector comprising the nucleic acid sequence, which encodes the E6/E7 polynucleotide, of SEQ ID NO: 7, or SEQ ID NO: 13, having optimization of codons, and substitution of nucleic acids encoding some amino acids.

The recombinant vector comprising the nucleic acid sequence of SEQ ID NO: 7, or SEQ ID NO: 13 of the present invention can further comprise a secretory signal sequence, and an amino acid sequence encoding an immune enhancing peptide. Examples of the secretory signal sequence include the secretory signal sequences of tPA, HSV, gDs, and a growth hormone, preferably secretory signal sequences used in higher eukaryotes such as a mammal, and more preferably tPa (tissue plasminogen activator). Examples of the above-mentioned sequence encoding the immune enhancing peptide include amino acid sequences encoding a CD40 ligand, an Flt3 ligand, a Flagellin, and OX40. At least one immune enhancing peptide can be selected from the above-listed peptides to use, and preferably the peptide can be selected individually to use. In the specific embodiments of the present invention, the CD40 ligand and the Flt3 ligand are used individually or in a combination thereof. Further, the secretory signal sequence and the nucleic acid sequence encoding the immune enhancing peptide are preferably substituted with a codon having a high expression frequency in a host cell. In specific embodiments, tPa contains the nucleic acid sequence of SEQ ID NO: 1, the Flt3 ligand contains the nucleic acid sequence of SEQ ID NO: 15, and the CD40 ligand contains the nucleic acid sequence of SEQ ID NO: 17.

In another embodiment, the recombinant vector of the present invention can be used for production of the fusion protein of the present invention, as a vector for gene transfer for gene therapy, or as a pharmaceutically active ingredient to be administered to a subject as it is.

Still another embodiment of the present invention relates to a pharmaceutical composition for the treatment and prevention of a disease caused by a human papilloma virus in a subject, comprising the fusion protein of the present invention and a pharmaceutically acceptable carrier. In the present invention, examples of the subject include a mammal, such as a human, a monkey, and a mouse, but are not limited thereto. Examples of the diseases caused by the virus include cervical cancer, condyloma acuminata, and wart.

Examples of the pharmaceutically acceptable carrier used in the composition of the present invention include lactose, glucose, sucrose, sorbitol, mannitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil. The composition may additionally include a lubricant, a wetting agent, a flavoring agent, an emulsifier, a preservative, and the like.

The composition of the present invention can be administered to a subject by any of various routes including intravenous, intramuscular, oral, transdermal, transcutaneous, intranasal, intratracheal, and subcutaneous administrations, but not limited thereto. The composition of the present invention can be indirectly administered into a subject by administering the composition into a cell cultured in vitro, and then administering the cultured cell into a body of the subject. The composition of the present invention can be administered systematically or topically.

The composition of the present invention may be formulated into oral dosage forms including, but not limited to, granules, powders, solutions, tablets, capsules, dry syrup and the like, or parenteral dosage forms including injectables. The composition of the present invention is preferably in the dosage form of solutions or injectables.

The effective amount of the fusion protein of the present invention as the active ingredient may range from about 0.05 to 500 mg/kg body weight, preferably 0.5 to 50 mg/kg body weight, and can be administered in a single dose or in divided doses. However, it should be understood that the amount of the active ingredient administered should be determined in light of various relevant factors including the condition to be treated, the age and weight of a patient, and the severity of the patient's symptom; and, therefore, the above dose should not be construed to limit the scope of the invention in any way.

Still another embodiment of the present invention relates to a pharmaceutical composition for the treatment and prevention of a disease caused by a human papilloma virus in a subject, comprising the recombinant vector of the present invention and a pharmaceutically acceptable carrier. In the present invention, examples of the subject include a mammal, such as a human, a monkey, and a mouse, but are not limited thereto. Examples of the diseases caused by the virus include cervical cancer, condyloma acuminata, and wart.

Examples of the pharmaceutically acceptable carrier used in the composition of the present invention include lactose, dextrose, sucrose, sorbitol, mannitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil. The composition may additionally include a lubricant, a wetting agent, a flavoring agent, an emulsifier, a preservative, and the like.

The composition of the present invention can be administered to a subject by any of various routes including intravenous, intramuscular, oral, transdermal, transcutaneous, intranasal, intratracheal, and subcutaneous administrations, but not limited thereto. The composition of the present invention can be indirectly administered into a subject by administering the composition into a cell cultured in vitro, and then administering the cultured cell into a body of the subject. The composition of the present invention can be administered systematically or topically.

The composition of the present invention may be formulated into oral dosage forms including but not limited to, granules, powders, solutions, tablets, capsules, dry syrup and the like, or parenteral dosage forms including injectables. The composition of the present invention is preferably in the dosage form of solutions or injectables.

The effective amount of the fusion protein of the present invention as the active ingredient may range from about 0.05 to 500 mg/kg body weight, preferably 0.5 to 50 mg/kg body weight, and can be administered in a single dose or in divided doses. However, it should be understood that the amount of the active ingredient administered should be determined in light of various relevant factors including the condition to be treated, the age and weight of a patient, and the severity of the patient's symptom; and, therefore, the above dose should not be construed to limit the scope of the invention in any way.

Still another embodiment of the present invention relates to a method for the treatment of a disease caused by a human papilloma virus in a subject, comprising a step of administering a therapeutically effective amount of the pharmaceutical composition of the present invention to the subject.

The pharmaceutical composition of the present invention, the efficacy, administration mode and administration amount of the composition are as described above. In the method of the present invention, examples of the subject include a mammal, such as a human, a monkey, a mouse, a pig, a cow, and a rabbit, but are not limited thereto.

Hereinbelow, the present invention will be described with reference to Examples. However, Examples are provided only for the purpose of illustrating the present invention, and the scope of the present invention is not intended to be limited to Examples.

[Mode for Invention]

EXAMPLE 1

Construction of pGX10/tE67$^{Co}$ DNA

The abbreviations used in Examples of the present invention have the following definitions:

"Co" means a codon-optimized nucleic acid sequence; "tPa" or "t" means a secretory signal sequence of a tissue plasminogen activator; "F" means a Flt3 ligand; and a "L" means a CD40 ligand.

The codon-optimized tPa secretory signal sequence containing the nucleic acid sequence of SEQ ID NO: 1 was synthesized chemically. To the ends, EcoRI-KpnI (5') and Eco47III-NheI (3') sites were added. The codon-optimized HPV16E6E7 containing the nucleic acid sequence of SEQ ID NO: 7 was synthesized chemically, and to the ends, Eco47III-NheI (5') and AscI-XhoI (3') sites were added to facilitate insertion into the vector. Further, to the junction of E6 and E7, a BamHI site was added. In order to eliminate the property of causing oncogenicity, in E6, the 63rd codon (cystein) was substituted with glycine; and the 106th codon (cystein) was substituted with a codon designating glycine (SEQ ID NO: 3). In E7, the 24th codon (cystein) was substituted with glycine; and the 26th codon (glutamine) was substituted with a codon designating glycine (SEQ ID NO: 5). A vector for the preparation of a DNA vaccine, pGX10 (in Korean Patent Application Publication No. 2003-0047667), was treated with EcoRI and NheI enzymes to link with the synthesized secretory signal sequence, tPa, using a ligase. The resultant was cleaved using NheI and XhoI enzymes to link with HPV16E6E7 using a ligase, to prepare pGX10/tE67$^{Co}$.

EXAMPLE 2

Construction of pGX10/tF$^{Co}$E67$^{Co}$ DNA

The codon-optimized tPa secretory signal sequence containing the nucleic acid sequence of SEQ ID NO: 1, and the codon-optimized Flt3L containing the nucleic acid sequence of SEQ ID NO: 15 were synthesized chemically in the linked form. To the ends, KpnI (5') and EcoRV (3') sites were added to facilitate insertion into the vector. The pGX10/tE67$^{Co}$ prepared in Example 1 was treated with KpnI and Eco47III enzymes, and only the secretory signal sequence, tPa, was removed. Then, tF$^{Co}$ was linked using a ligase, to prepare pGX10/tF$^{Co}$E67$^{Co}$.

EXAMPLE 3

Construction of pGX10/tE67$^{Co}$L$^{Co}$ DNA

The codon-optimized CD40L containing the nucleic acid sequence of SEQ ID NO: 17 was synthesized chemically. To the ends, AscI (5'), and XhoI (3') sites were added to facilitate insertion into the vector. The pGX10/tE67$^{Co}$ prepared in Example 1 was treated with AscI and XhoI enzymes, and the CD40L$^{Co}$ was linked using a ligase, to prepare pGX10/tE67$^{Co}$L$^{Co}$.

EXAMPLE 4

Confirmation of Effects of Prevention of Cervical Cancer of pGX10/tE67$^{Co}$, pGX10/tF$^{Co}$E67$^{Co}$, and pGX10/tE67$^{Co}$L$^{Co}$ To confirm the effects of prevention of cervical cancer of pGX10/tE67$^{Co}$, pGX10/tF$^{Co}$E67$^{Co}$, and pGX10/tE67$^{Co}$L$^{Co}$, they were intramuscularly injected to a mouse C57BL/6, respectively, twice in an amount of 50 μg every fourth week, and pGX10, pGX10/E6$^{Co}$, pGX10/E7$^{Co}$, pGX10/E67$^{Co}$, and pGX10/E67 were intramuscularly injected to as the control groups in the same amount at the same interval. The spleen was taken out from the mouse at 6.5 weeks after initial intramuscular injection, and to a plate which had been coated with 50 μL of an anti-mouse IFN-γ antibody (BD Pharmingen, San Diego, Calif.) at 3 μg/ml, was put 1×10$^6$ cells, together with IL-2, and E6 or E7 CD8 T cell epitopes (E6$_{48-57}$; EVYD-FAFRDL, E7$_{49-57}$; RAHYNIVTF, Peptron, Korea). They were cultured in an incubator (Forma, Minn., USA) at 37° C. and 5% CO$_2$ for 24 hours. The plate was washed with PBST, and then 50 μL of an IFN-γ detecting antibody (BD Pharmingen, San Diego, Calif.) having a pendent biotin at 2 μg/mL was put thereto, and it was cultured at ambient temperature for about 3 hours. Thereafter, it was washed with PBST, and 50 μL of streptavidin-AKP (alkaline phosphate) which had been diluted to 1:2000 was added thereto, and the resultant was cultured at ambient temperature for 1 hour. It was washed with PBST, and then 50 μL of the mixture of 66 μL of NBT (Promega, Madison, WT) and 33 μL of BCIP (Promega, Madison, WT) in 10 mL of an alkaline phosphate buffer was added to the resultant to be reacted with each other. To obtain clear color expression by the reaction, the product was put into an incubator at 37° C. for about 30 min, and washed with distilled water (D. W), and the number of the generated spots was recorded by a reader (see FIGS. 1 and 2).

Using an E6 CD8 T cell epitope and an E7 CD8 T cell epitope, an E6/E7-specific T cell immune response was measured using ELISPOT, and as a result, it was found that pGX10/E67$^{Co}$ induced a higher degree of the antigen-specific immune response than pGX10/E67, indicating that codon-optimization is more effective for enhancing the antigen-specific immune response. Further, it was found that pGX10/tE67$^{Co}$ induced a higher degree of the CD8 T cell immune response than pGX10/E67$^{Co}$, indicating that the secretory signal sequence, tPa, is also effective for improving the antigen-specific immune response. Further, it was found that pGX10/tE67$^{Co}$L$^{Co}$ induced a lower degree of the E6 specific immune response than pGX10/tE67$^{Co}$, but induced substantially the same degree of the E7 specific response, as compared with the other control groups, indicating that it is effective for enhancing the immune response. It was confirmed that pGX10/tFE67$^{Co}$ is most effective for induction of the E6- and E7-specific immune response.

At 6.5 weeks after initial injection, a tumor cell expressing the HPV16 E6 and E7, TC-1, was subcutaneously injected to a subject at 5×10$^5$ cells, and the increase in the volumes of the tumor cell was measured (see FIG. 3). Particularly, in the E6- and E7-specific immune response, the fusion product, E67$^{Co}$ induced a lower degree of the immune response, as compared with each of the E6$^{Co}$ and E7$^{Co}$ (see FIGS. 1 and 2), but showed a higher anti-cancer effect to the injected TC-1 tumor cell. This indicates that the E67 fusion product is better for the anti-cancer effect, since it can induce the immune responses against two tumor antigens, E6 and E7, simultaneously, rather than the individual immune response against one of them even though the response is strong. It was observed that tumor did not occur in the mouse which had been injected with pGX10/tE67$^{Co}$, pGX10/tF$^{Co}$E67$^{Co}$, and pGX10/tE67$^{Co}$L$^{Co}$ by day 24 after injection of a tumor cell, but the volume of a tumor was drastically increased in the other control group from the time point of day 9 after injection of a tumor cell. Therefore, it can be confirmed that pGX10/tE67$^{Co}$, pGX10/tF$^{Co}$E67$^{Co}$, and pGX10/tE67$^{Co}$L$^{Co}$ have higher ability of preventing cervical cancer.

EXAMPLE 5

Confirmation of Effects of Treatment of Cervical Cancer of pGX10/tE67$^{Co}$, pGX10/tF$^{Co}$E67$^{Co}$, pGX10/tE67$^{Co}$L$^{Co}$ To confirm the effects of treatment of cervical cancer of pGX10/tE67$^{Co}$, pGX10/tF$^{Co}$E67$^{Co}$, pGX10/tE67$^{Co}$L$^{Co}$, the TC-1 tumor cells were subcutaneously injected to a mouse C57BL/6 at 5×10$^5$ cells, respectively, and further muscularly injected in an amount of 50 μg at days 3, and 8 after initiating the injection of TC-1 tumor cells. Starting from the day when injection of the tumor cells (day 0), the change in the volumes of tumor mass was observed to day 21, and at day 22, the spleen was taken out from the mouse, and the degrees of induction of a CD8 T cell immune response which is specific to the antigens against E6 and E7 were measured in the same manner (ELISPOT) as described in Example 4. As compared with pGX10 as the control group, a higher degree of the antigen-specific immune response was induced in the mice treated with pGX10/tE67$^{Co}$, pGX10/tF$^{Co}$E67$^{Co}$, and pGX10/tE67$^{Co}$L$^{Co}$, and particularly a highest degree of the immune response was measured in the mouse treated with pGX10/ tF<sup>Co</sup>E67<sup>Co</sup>, indicating that pGX10/tF<sup>Co</sup>E67<sup>Co</sup> has a high efficacy of inducing an anti-cancer immune response (see FIGS. 4 and 5).

It was found that the mice which had been immune-treated with pGX10/tE67<sup>Co</sup>, pGX10/tF<sup>Co</sup>E67<sup>Co</sup>, and pGX10/tE67<sup>Co</sup>L<sup>Co</sup> against the TC-1 tumor cells showed significant reduction in the volume of a tumor, as compared with the mouse treated with pGX10, as the control group. Further, it was found that the volume of a tumor was continuously increased until day 12 after injection of the tumor cells, and then after that, the volume started to decrease, and particularly it was found that in the mice which had been immune-treated with pGX10/tF<sup>Co</sup>E67<sup>Co</sup> and pGX10/tE67<sup>Co</sup>L<sup>Co</sup>, the volume of a tumor was substantially zero at day 21, indicating that it has an effect of treatment of cervical cancer (see FIG. 6).

---

The invention claimed is:

1. A fusion protein comprising a fusion polypeptide of E6 and E7 of a human papilloma virus type 16 (HPV16), a signal peptide tPa (tissue plasminogen activator), and an immune enhancing peptide Flt3 (fms-like tyrosine kinase receptor-3) ligand for a subject, wherein the fusion polypeptide of E6 and E7 has the amino acid sequence of SEQ ID NO: 8 or SEQ ID NO: 14.

2. The fusion protein according to claim 1, wherein tPa has the amino acid sequence of SEQ ID NO: 2.

3. The fusion protein according to claim 1, wherein the Flt3 ligand has the amino acid sequence of SEQ ID NO: 16.

4. A pharmaceutical composition for the treatment and prevention of a disease caused by a human papilloma virus in a subject, comprising the fusion protein of claim 1 and a pharmaceutically acceptable carrier.

* * * * *

SEQUENCE LISTING

```
<160> NUMBER OF SEQ ID NOS: 18

<210> SEQ ID NO 1
<211> LENGTH: 75
<212> TYPE: DNA
<213> ORGANISM: Artificial Sequence
<220> FEATURE:
<223> OTHER INFORMATION: codon optimized signal sequence of tissue
      plasminogen activator

<400> SEQUENCE: 1
atggacgcca tgaagcgcgg cctgtgctgc gtgctgctgc tgtgcggcgc cgtgtttgtg     60
agccccagcg ctagc                                                     75

<210> SEQ ID NO 2
<211> LENGTH: 75
<212> TYPE: PRT
<213> ORGANISM: Artificial Sequence
<220> FEATURE:
<223> OTHER INFORMATION: tissue plasminogen activator

<400> SEQUENCE: 2

Ala Thr Gly Gly Ala Cys Gly Cys Cys Ala Thr Gly Ala Ala Gly Cys
  1               5                  10                  15

Gly Cys Gly Gly Cys Cys Thr Gly Thr Gly Cys Thr Gly Cys Gly Thr
             20                  25                  30

Gly Cys Thr Gly Cys Thr Gly Cys Thr Gly Thr Gly Cys Gly Gly Cys
         35                  40                  45

Gly Cys Cys Gly Thr Gly Thr Thr Thr Gly Thr Gly Ala Gly Cys Cys
     50                  55                  60

Cys Cys Ala Gly Cys Gly Cys Thr Ala Gly Cys
 65                  70                  75

<210> SEQ ID NO 3
<211> LENGTH: 477
<212> TYPE: DNA
<213> ORGANISM: Artificial Sequence
<220> FEATURE:
<223> OTHER INFORMATION: codon optimized and mutated HPV16 E6

<400> SEQUENCE: 3
atgcaccaga agcggaccgc tatgtttcag gaccctcagg aacggcctcg gaaactgcct     60
cagctgtgca ccgagctgca gaccaccatc cacgacatca tcctggagtg cgtgtactgc    120
aaacagcagc tgctccggcg ggaggtgtac gacttcgctt tcgggatctg tgcatcgtg     180 taccgggacg gcaacccata tgctgtgggc gacaagtgtt taaagttcta cagcaagatc    240
agcgagtacc ggcactactg ctacagcctg tacggcacca ccctggagca gcagtacaac    300
aaacctctgt gcgacctgct catccggtgc atcaatggcc agaaacctct gtgccctgag    360
gaaaagcagc ggcacctgga caagaaacag cggtttcaca atatccgggg ccggtggacc    420
ggccggtgca tgagctgctg ccggagcagc cggacccggc gggaaaccca gctgtga       477
```

<210> SEQ ID NO 4
<211> LENGTH: 477
<212> TYPE: PRT
<213> ORGANISM: Artificial Sequence
<220> FEATURE:
<223> OTHER INFORMATION: HPV16 E6

<400> SEQUENCE: 4

```
Ala Thr Gly Cys Ala Cys Cys Ala Gly Ala Ala Gly Cys Gly Gly Ala
 1               5                  10                  15

Cys Cys Gly Cys Thr Ala Thr Gly Thr Thr Cys Ala Gly Gly Ala
            20                  25                  30

Cys Cys Cys Thr Cys Ala Gly Gly Ala Ala Cys Gly Gly Cys Cys Thr
        35                  40                  45

Cys Gly Gly Ala Ala Ala Cys Thr Gly Cys Cys Thr Cys Ala Gly Cys
        50                  55                  60

Thr Gly Thr Gly Cys Ala Cys Gly Ala Gly Cys Thr Gly Cys Ala
 65                  70                  75                  80

Gly Ala Cys Cys Ala Cys Cys Ala Thr Cys Cys Ala Cys Gly Ala Cys
                85                  90                  95

Ala Thr Cys Ala Thr Cys Cys Thr Gly Gly Ala Gly Thr Gly Cys Gly
                100                 105                 110

Thr Gly Thr Ala Cys Thr Gly Cys Ala Ala Cys Ala Gly Cys Ala
            115                 120                 125

Gly Cys Thr Gly Cys Thr Cys Gly Gly Cys Gly Gly Gly Ala Gly
            130                 135                 140

Gly Thr Gly Thr Ala Cys Gly Ala Cys Thr Thr Cys Gly Cys Thr Thr
145                 150                 155                 160

Thr Thr Cys Gly Gly Gly Ala Thr Cys Thr Gly Thr Gly Cys Ala Thr
                165                 170                 175

Cys Gly Thr Gly Thr Ala Cys Cys Gly Gly Gly Ala Cys Gly Gly Cys
            180                 185                 190

Ala Ala Cys Cys Cys Ala Thr Ala Thr Gly Cys Thr Gly Thr Gly Gly
            195                 200                 205

Gly Cys Gly Ala Cys Ala Ala Gly Thr Gly Thr Thr Ala Ala Ala
            210                 215                 220

Gly Thr Thr Cys Thr Ala Cys Ala Gly Cys Ala Ala Gly Ala Thr Cys
225                 230                 235                 240

Ala Gly Cys Gly Ala Gly Thr Ala Cys Cys Gly Gly Cys Ala Cys Thr
                245                 250                 255

Ala Cys Thr Gly Cys Thr Ala Cys Ala Gly Cys Cys Thr Gly Thr Ala
                260                 265                 270

Cys Gly Gly Cys Ala Cys Cys Ala Cys Cys Cys Thr Gly Gly Ala Gly
            275                 280                 285

Cys Ala Gly Cys Ala Gly Thr Ala Cys Ala Ala Cys Ala Ala Ala Cys
            290                 295                 300

Cys Thr Cys Thr Gly Thr Gly Cys Gly Ala Cys Cys Thr Gly Cys Thr
305                 310                 315                 320

Cys Ala Thr Cys Cys Gly Gly Thr Gly Cys Ala Thr Cys Ala Ala Thr
                325                 330                 335

Gly Gly Cys Cys Ala Gly Ala Ala Ala Cys Cys Thr Cys Thr Gly Thr
                340                 345                 350

Gly Cys Cys Cys Thr Gly Ala Gly Gly Ala Ala Ala Gly Cys Ala
            355                 360                 365
```

-continued

```
Gly Cys Gly Gly Cys Ala Cys Cys Thr Gly Gly Ala Cys Ala Ala Gly
        370                 375                 380

Ala Ala Ala Cys Ala Gly Cys Gly Gly Thr Thr Cys Ala Cys Ala
385                 390                 395                 400

Ala Thr Ala Thr Cys Cys Gly Gly Gly Cys Cys Gly Gly Thr Gly
                405                 410                 415

Gly Ala Cys Cys Gly Gly Cys Cys Gly Gly Thr Gly Cys Ala Thr Gly
            420                 425                 430

Ala Gly Cys Thr Gly Cys Thr Gly Cys Gly Gly Ala Gly Cys Ala
        435                 440                 445

Gly Cys Cys Gly Gly Ala Cys Cys Cys Gly Gly Cys Gly Gly Gly Ala
        450                 455                 460

Ala Ala Cys Cys Cys Ala Gly Cys Thr Gly Thr Gly Ala
465                 470                 475

<210> SEQ ID NO 5
<211> LENGTH: 297
<212> TYPE: DNA
<213> ORGANISM: Artificial Sequence
<220> FEATURE:
<223> OTHER INFORMATION: codon optimized and mutated HPV16 E7

<400> SEQUENCE: 5
atgcacggcg ataccccac cctgcacgag tacatgctgg atctgcagcc tgaaaccacc      60
gatctgtacg gctacggcca gctgaacgac agctccgagg aagaagatga aatcgatggc     120
cctgctggcc aggctgaacc tgaccgggcc cactacaaca tcgtgacctt ctgctgcaaa     180
tgcgatagca ccctgcggct gtgcgtgcag agcacccacg tagacatccg gaccctggag     240
gatctgctca tgggcaccct gggcatcgtg tgccctatct gcagccagaa accttga       297

<210> SEQ ID NO 6
<211> LENGTH: 297
<212> TYPE: PRT
<213> ORGANISM: Artificial Sequence
<220> FEATURE:
<223> OTHER INFORMATION: HPV16 E7

<400> SEQUENCE: 6

Ala Thr Gly Cys Ala Cys Gly Gly Cys Gly Ala Thr Ala Cys Cys Cys
1                   5                   10                  15

Cys Cys Ala Cys Cys Cys Thr Gly Cys Ala Cys Gly Ala Gly Thr Ala
                20                  25                  30

Cys Ala Thr Gly Cys Thr Gly Gly Ala Thr Cys Thr Gly Cys Ala Gly
            35                  40                  45

Cys Cys Thr Gly Ala Ala Ala Cys Cys Ala Cys Cys Gly Ala Thr Cys
        50                  55                  60

Thr Gly Thr Ala Cys Gly Gly Cys Thr Ala Cys Gly Gly Cys Cys Ala
65                  70                  75                  80

Gly Cys Thr Gly Ala Ala Cys Gly Ala Cys Ala Gly Cys Thr Cys Cys
                85                  90                  95

Gly Ala Gly Gly Ala Ala Gly Ala Ala Gly Ala Thr Gly Ala Ala
            100                 105                 110

Thr Cys Gly Ala Thr Gly Gly Cys Cys Thr Gly Cys Thr Gly Gly
        115                 120                 125

Cys Cys Ala Gly Gly Cys Thr Gly Ala Ala Cys Thr Gly Ala Cys
    130                 135                 140

Cys Gly Gly Gly Cys Cys Cys Ala Cys Thr Ala Cys Ala Ala Cys Ala
145                 150                 155                 160
```

Thr Cys Gly Thr Gly Ala Cys Cys Thr Cys Thr Gly Cys Thr Gly
                165                 170                 175

Cys Ala Ala Ala Thr Gly Cys Gly Ala Thr Ala Gly Cys Ala Cys Cys
                180                 185                 190

Cys Thr Gly Cys Gly Gly Cys Thr Gly Thr Gly Cys Gly Thr Gly Cys
                195                 200                 205

Ala Gly Ala Gly Cys Ala Cys Cys Cys Ala Cys Gly Thr Ala Gly Ala
    210                 215                 220

Cys Ala Thr Cys Cys Gly Gly Ala Cys Cys Cys Thr Gly Gly Ala Gly
225                 230                 235                 240

Gly Ala Thr Cys Thr Gly Cys Thr Cys Ala Thr Gly Gly Gly Cys Ala
                245                 250                 255

Cys Cys Cys Thr Gly Gly Gly Cys Ala Thr Cys Gly Thr Gly Thr Gly
                260                 265                 270

Cys Cys Cys Thr Ala Thr Cys Thr Gly Cys Ala Gly Cys Cys Ala Gly
                275                 280                 285

Ala Ala Ala Cys Cys Thr Thr Gly Ala
                290                 295

<210> SEQ ID NO 7
<211> LENGTH: 789
<212> TYPE: DNA
<213> ORGANISM: Artificial Sequence
<220> FEATURE:
<223> OTHER INFORMATION: codon optimized and mutated HPV16 E6E7

<400> SEQUENCE: 7
atgcaccaga agcggaccgc tatgtttcag gaccctcagg aacggcctcg gaaactgcct      60
cagctgtgca ccgagctgca gaccaccatc cacgacatca tcctggagtg cgtgtactgc     120
aaacagcagc tgctccggcg ggaggtgtac gacttcgctt ttcgggatct gtgcatcgtg     180
taccgggacg gcaacccata tgctgtgggc gacaagtgtt taaagttcta cagcaagatc     240
agcgagtacc ggcactactg ctacagcctg tacggcacca ccctggagca gcagtacaac     300
aaacctctgt cgacctgct catccggtgc atcaatggcc agaaacctct gtgccctgag     360
gaaaagcagc ggcacctgga caagaaacag cggtttcaca atatccgggg ccggtggacc     420
ggccggtgca tgagctgctg ccggagcagc cggacccggc gggaaaccca gctgggaagc     480
ggatccggca gcatgcacgg cgataccccc accctgcacg agtacatgct ggatctgcag     540
cctgaaacca ccgatctgta cggctacggc cagctgaacg acagctccga ggaagaagat     600
gaaatcgatg gccctgctgg ccaggctgaa cctgaccggg cccactacaa catcgtgacc     660
ttctgctgca atgcgatag caccctgcgc ctgtgcgtgc agagcaccca cgtagacatc     720
cggaccctgg aggatctgct catgggcacc ctgggcatcg tgtgccctat ctgcagccag     780
aaaccttga                                                             789

<210> SEQ ID NO 8
<211> LENGTH: 789
<212> TYPE: PRT
<213> ORGANISM: Artificial Sequence
<220> FEATURE:
<223> OTHER INFORMATION: HPV16 E6E7

<400> SEQUENCE: 8

Ala Thr Gly Cys Ala Cys Cys Ala Gly Ala Ala Gly Cys Gly Gly Ala
 1               5                  10                  15

Cys Cys Gly Cys Thr Ala Thr Gly Thr Thr Thr Cys Ala Gly Gly Ala

```
                20                  25                  30
Cys Cys Cys Thr Cys Ala Gly Gly Ala Ala Cys Gly Gly Cys Cys Thr
                35                  40                  45
Cys Gly Gly Ala Ala Ala Cys Thr Gly Cys Cys Thr Cys Ala Gly Cys
        50                  55                  60
Thr Gly Thr Gly Cys Ala Cys Cys Gly Ala Gly Cys Thr Gly Cys Ala
65                  70                  75                  80
Gly Ala Cys Cys Ala Cys Cys Ala Thr Cys Ala Cys Gly Ala Cys
                85                  90                  95
Ala Thr Cys Ala Thr Cys Cys Thr G

-continued

Gly Cys Cys Gly Gly Ala Cys Cys Gly Cys Gly Gly Ala
         450                 455                 460

Ala Ala Cys Cys Cys Ala Gly Cys Thr Gly Gly Ala Gly Cys
465                 470                 475                 480

Gly Gly Ala Thr Cys Cys Gly Cys Ala Gly Cys Ala Thr Gly Cys
             485                 490                 495

Ala Cys Gly Gly Cys Gly Ala Thr Ala Cys Cys Cys Ala Cys
             500                 505                 510

Cys Cys Thr Gly Cys Ala Cys Gly Ala Gly Thr Ala Cys Ala Thr Gly
         515                 520                 525

Cys Thr Gly Gly Ala Thr Cys Thr Gly Cys Ala Gly Cys Cys Thr Gly
         530                 535                 540

Ala Ala Ala Cys Cys Ala Cys Cys Gly Ala Thr Cys Thr Gly Thr Ala
545                 550                 555                 560

Cys Gly Gly Cys Thr Ala Cys Gly Gly Cys Cys Ala Gly Cys Thr Gly
             565                 570                 575

Ala Ala Cys Gly Ala Cys Ala Gly Cys Thr Cys Cys Gly Ala Gly Gly
             580                 585                 590

Ala Ala Gly Ala Ala Gly Ala Thr Gly Ala Ala Thr Cys Gly Ala
         595                 600                 605

Thr Gly Gly Cys Cys Cys Thr Gly Cys Thr Gly Gly Cys Cys Ala Gly
         610                 615                 620

Gly Cys Thr Gly Ala Cys Cys Thr Gly Ala Cys Cys Gly Gly Gly
625                 630                 635                 640

Cys Cys Cys Ala Cys Thr Ala Cys Ala Ala Cys Ala Thr Cys Gly Thr
             645                 650                 655

Gly Ala Cys Cys Thr Thr Cys Thr Gly Cys Thr Gly Cys Ala Ala Ala
             660                 665                 670

Thr Gly Cys Gly Ala Thr Ala Gly Cys Ala Cys Cys Cys Thr Gly Cys
         675                 680                 685

Gly Gly Cys Thr Gly Thr Gly Cys Gly Thr Gly Cys Ala Gly Ala Gly
         690                 695                 700

Cys Ala Cys Cys Cys Ala Cys Gly Thr Ala Gly Ala Cys Ala Thr Cys
705                 710                 715                 720

Cys Gly Gly Ala Cys Cys Cys Thr Gly Gly Ala Gly Ala Thr Cys
             725                 730                 735

Thr Gly Cys Thr Cys Ala Thr Gly Gly Cys Ala Cys Cys Cys Thr
         740                 745                 750

Gly Gly Gly Cys Ala Thr Cys Thr Gly Thr Gly Cys Cys Cys Thr
         755                 760                 765

Ala Thr Cys Thr Gly Cys Ala Gly Cys Cys Ala Gly Ala Ala Ala Cys
770                 775                 780

Cys Thr Thr Gly Ala
785

<210> SEQ ID NO 9
<211> LENGTH: 555
<212> TYPE: DNA
<213> ORGANISM: Artificial Sequence
<220> FEATURE:
<223> OTHER INFORMATION: codon optimized and mutated HPV18 E6

<400> SEQUENCE: 9
atggacgcca tgaagagggg cctgtgctgc gtgctgctgc tgtgcggcgc cgtgttcgtg      60
agccccagcg ctagcgctat ggcgcgcttt gaggatccaa cacggcgacc ctacaagcta     120

-continued

```
cctgatctgt gcacggaact gaacacttca ctgcaagaca tagaaataac ctgtgtatat    180
tgcaagacag tattggaact tacagaggta tttgaatttg catttaaaga tttatttgtg    240
gtgtatagag acagtatacc gcatgctgca ggccataaat gtatagattt ttattctaga    300
attagagaat taagcatta ttcagactct gtgtatggag acacattgga aaaactaact    360
aacactgggt tatacaattt attaataagg tgcctgcggg gtcagaaacc gttgaatcca    420
gcagaaaaac ttagcacct taatgaaaaa cgacgatttc acaacatagc tgggcactat    480
agaggccagt gccattcgtg ctgcaaccga gcacgacagg aaagactcca acgacgcaga    540
gaaacacaag tatga                                                    555
```

<210> SEQ ID NO 10
<211> LENGTH: 555
<212> TYPE: PRT
<213> ORGANISM: Artificial Sequence
<220> FEATURE:
<223> OTHER INFORMATION: HPV18 E6

<400> SEQUENCE: 10

```
Ala Thr Gly Gly Ala Cys Gly Cys Ala Thr Gly Ala Gly Ala
 1               5                  10                  15

Gly Gly Gly Gly Cys Cys Thr Gly Thr Gly Cys Thr Gly Cys Gly Thr
                20                  25                  30

Gly Cys Thr Gly Cys Thr Gly Cys Thr Gly Thr Gly Cys Gly Gly Cys
            35                  40                  45

Gly Cys Cys Gly Thr Gly Thr Thr Cys Gly Thr Gly Ala Gly Cys Cys
        50                  55                  60

Cys Cys Ala Gly Cys Gly Cys Thr Ala Gly Cys Gly Cys Thr Ala Thr
65                  70                  75                  80

Gly Gly Cys Gly Cys Gly Cys Thr Thr Thr Gly Ala Gly Gly Ala Thr
                85                  90                  95

Cys Cys Ala Ala Cys Ala Cys Gly Gly Cys Gly Ala Cys Cys Cys Thr
                100                 105                 110

Ala Cys Ala Ala Gly Cys Thr Ala Cys Cys Thr Gly Ala Thr Cys Thr
                115                 120                 125

Gly Thr Gly Cys Ala Cys Gly Gly Ala Ala Cys Thr Gly Ala Ala Cys
            130                 135                 140

Ala Cys Thr Thr Cys Ala Cys Thr Gly Cys Ala Ala Gly Ala Cys Ala
145                 150                 155                 160

Thr Ala Gly Ala Ala Ala Thr Ala Ala Cys Cys Thr Gly Thr Gly Thr
                165                 170                 175

Ala Thr Ala Thr Thr Gly Cys Ala Ala Gly Ala Cys Ala Gly Thr Ala
                180                 185                 190

Thr Thr Gly Gly Ala Ala Cys Thr Thr Ala Cys Ala Gly Ala Gly Gly
            195                 200                 205

Thr Ala Thr Thr Thr Gly Ala Ala Thr Thr Thr Gly Cys Ala Thr Thr
        210                 215                 220

Thr Ala Ala Ala Gly Ala Thr Thr Thr Ala Thr Thr Thr Gly Thr Gly
225                 230                 235                 240

Gly Thr Gly Thr Ala Thr Ala Gly Ala Gly Ala Cys Ala Gly Thr Ala
                245                 250                 255

Thr Ala Cys Cys Gly Cys Ala Thr Gly Cys Thr Gly Cys Ala Gly Gly
                260                 265                 270

Cys Cys Ala Thr Ala Ala Ala Thr Gly Thr Ala Thr Ala Gly Ala Thr
            275                 280                 285
```

Thr Thr Thr Thr Ala Thr Thr Cys Thr Ala Gly Ala Ala Thr Thr Ala
  290                 295                 300
Gly Ala Gly Ala Ala Thr Ala Ala Gly Ala Cys Ala Thr Thr Ala
305                 310                 315                 320
Thr Thr Cys Ala Gly Ala Cys Thr Cys Thr Gly Thr Gly Thr Ala Thr
                325                 330                 335
Gly Gly Ala Gly Ala Cys Ala Cys Ala Thr Gly Gly Ala Ala Ala
                340                 345                 350
Ala Ala Cys Thr Ala Ala Cys Thr Ala Ala Cys Ala Cys Thr Gly Gly
            355                 360                 365
Gly Thr Thr Ala Thr Ala Cys Ala Ala Thr Thr Ala Thr Thr Ala
370                 375                 380
Ala Thr Ala Ala Gly Gly Thr Gly Cys Cys Thr Gly Cys Gly Gly
385                 390                 395                 400
Gly Thr Cys Ala Gly Ala Ala Ala Cys Cys Gly Thr Thr Gly Ala Ala
                405                 410                 415
Thr Cys Cys Ala Gly Cys Ala Gly Ala Ala Ala Ala Cys Thr Thr
                420                 425                 430
Ala Gly Ala Cys Ala Cys Cys Thr Thr Ala Ala Thr Gly Ala Ala Ala
            435                 440                 445
Ala Ala Cys Gly Ala Cys Gly Ala Thr Thr Thr Cys Ala Cys Ala Ala
450                 455                 460
Cys Ala Thr Ala Gly Cys Thr Gly Gly Gly Cys Ala Cys Thr Ala Thr
465                 470                 475                 480
Ala Gly Ala Gly Gly Cys Cys Ala Gly Thr Gly Cys Cys Ala Thr Thr
                485                 490                 495
Cys Gly Thr Gly Cys Thr Gly Cys Ala Ala Cys Cys Gly Ala Gly Cys
                500                 505                 510
Ala Cys Gly Ala Cys Ala Gly Gly Ala Ala Gly Ala Cys Thr Cys
            515                 520                 525
Cys Ala Ala Cys Gly Ala Cys Gly Ala Cys Ala Gly Ala Gly Ala Ala Ala
            530                 535                 540
Cys Ala Cys Ala Ala Gly Thr Ala Thr Gly Ala
545                 550                 555

<210> SEQ ID NO 11
<211> LENGTH: 318
<212> TYPE: DNA
<213> ORGANISM: Artificial Sequence
<220> FEATURE:
<223> OTHER INFORMATION: codon optimized and mutated HPV18 E7

<400> SEQUENCE: 11
atgcatggac ctaaggcaac attgcaagac attgtattgc atttagagcc ccaaaatgaa    60
attccggttg accttctagg tcacgggcaa ttaagcgact cagaggaaga aaacgatgaa   120
atagatggag ttaatcatca acatttacca gcccgacgag ctgaaccaca acgtcacaca   180
atgttgtgta tgtgttgtaa gtgtgaagcc agaattgagc tagtagtaga aagctcagca   240
gacgaccttc gagcattcca gcagctgttt ctgaacaccc tgtcctttgt gtgtccgtgg   300
tgtgcatccc agcagtaa                                                 318

<210> SEQ ID NO 12
<211> LENGTH: 318
<212> TYPE: PRT
<213> ORGANISM: Artificial Sequence
<220> FEATURE:
<223> OTHER INFORMATION: HPV18 E7

-continued

<400> SEQUENCE: 12

Ala Thr Gly Cys Ala Thr Gly Gly Ala Cys Cys Thr Ala Ala Gly Gly
1 5 10 15

Cys Ala Ala Cys Ala Thr Thr Gly Cys Ala Ala Gly Ala Cys Ala Thr
20 25 30

Thr Gly Thr Ala Thr Thr Gly Cys Ala Thr Thr Thr Ala Gly Ala Gly
35 40 45

Cys Cys Cys Cys Ala Ala Ala Ala Thr Gly Ala Ala Ala Thr Thr Cys
50 55 60

Cys Gly Gly Thr Thr Gly Ala Cys Cys Thr Thr Cys Thr Ala Gly Gly
65 70 75 80

Thr Cys Ala Cys Gly Gly Gly Cys Ala Ala Thr Thr Ala Ala Gly Cys
85 90 95

Gly Ala Cys Thr Cys Ala Gly Ala Gly Gly Ala Ala Gly Ala Ala Ala
100 105 110

Ala Cys Gly Ala Thr Gly Ala Ala Ala Thr Ala Gly Ala Thr Gly Gly
115 120 125

Ala Gly Thr Thr Ala Ala Thr Cys Ala Thr Cys Ala Ala Cys Ala Thr
130 135 140

Thr Thr Ala Cys Cys Ala Gly Cys Cys Cys Gly Ala Cys Gly Ala Gly
145 150 155 160

Cys Thr Gly Ala Ala Cys Cys Ala Cys Ala Ala Cys Gly Thr Cys Ala
165 170 175

Cys Ala Cys Ala Ala Thr Gly Thr Thr Gly Thr Gly Thr Ala Thr Gly
180 185 190

Thr Gly Thr Thr Gly Thr Ala Ala Gly Thr Gly Thr Gly Ala Ala Gly
195 200 205

Cys Cys Ala Gly Ala Ala Thr Thr Gly Ala Gly Cys Thr Ala Gly Thr
210 215 220

Ala Gly Thr Ala Gly Ala Ala Ala Gly Cys Thr Cys Ala Gly Cys Ala
225 230 235 240

Gly Ala Cys Gly Ala Cys Cys Thr Thr Cys Gly Ala Gly Cys Ala Thr
245 250 255

Thr Cys Cys Ala Gly Cys Ala Gly Cys Thr Gly Thr Thr Thr Cys Thr
260 265 270

Gly Ala Ala Cys Ala Cys Cys Cys Thr Gly Thr Cys Cys Thr Thr Thr
275 280 285

Gly Thr Gly Thr Gly Thr Cys Cys Gly Thr Gly Gly Thr Gly Thr Gly
290 295 300

Cys Ala Thr Cys Cys Cys Ala Gly Cys Ala Gly Thr Ala Ala
305 310 315

<210> SEQ ID NO 13
<211> LENGTH: 888
<212> TYPE: DNA
<213> ORGANISM: Artificial Sequence
<220> FEATURE:
<223> OTHER INFORMATION: codon optimized and mutated HPV18 E6E7

<400> SEQUENCE: 13
atggacgcca tgaagagggg cctgtgctgc gtgctgctgc tgtgcggcgc cgtgttcgtg 60
agccccagcg ctagcgctat ggcgcgcttt gaggatccaa cacggcgacc ctacaagcta 120
cctgatctgt gcacggaact gaacacttca ctgcaagaca tagaaataac ctgtgtatat 180
tgcaagacag tattggaact tacagaggta tttgaatttg catttaaaga tttatttgtg 240

```
gtgtatagag acagtataccc gcatgctgca ggccataaat gtatagatttt ttattctaga    300 attagagaat taagacatta ttcagactct gtgtatggag acacattgga aaaactaact    360
aacactgggt tatacaattt attaataagg tgcctgcggg gtcagaaacc gttgaatcca    420
gcagaaaaac ttagacacct taatgaaaaa cgacgatttc acaacatagc tgggcactat    480
agaggccagt gccattcgtg ctgcaaccga gcacgacagg aaagactcca acgacgcaga    540
gaaacacaag taggatctgg atccggctcc atgcatggac ctaaggcaac attgcaagac    600
attgtattgc atttagagcc ccaaaatgaa attccggttg accttctagg tcacgggcaa    660
ttaagcgact cagaggaaga aaacgatgaa atagatggag ttaatcatca acatttacca    720
gcccgacgag ctgaaccaca acgtcacaca atgttgtgta tgtgttgtaa gtgtgaagcc    780
agaattgagc tagtagtaga aagctcagca gacgaccttc gagcattcca gcagctgttt    840
ctgaacaccc tgtcctttgt gtgtccgtgg tgtgcatccc agcagtaa                 888
```

```
<210> SEQ ID NO 14
<211> LENGTH: 888
<212> TYPE: PRT
<213> ORGANISM: Artificial Sequence
<220> FEATURE:
<223> OTHER INFORMATION: HPV18 E6E7

<400> SEQUENCE: 14

Ala Thr Gly Gly Ala Cys Gly Cys Cys Ala Thr Gly Ala Ala Gly Ala
  1               5                  10                  15

Gly Gly Gly Gly Cys Cys Thr Gly Thr Gly Cys Thr Cys Gly Thr
             20                  25                  30

Gly Cys Thr Gly Cys Thr Gly Cys Thr Gly Thr Gly Cys Gly Gly Cys
         35                  40                  45

Gly Cys Cys Gly Thr Gly Thr Thr Cys Gly Thr Gly Ala Gly Cys Cys
     50                  55                  60

Cys Cys Ala Gly Cys Gly Cys Thr Ala Gly Cys Gly Cys Thr Ala Thr
 65                  70                  75                  80

Gly Gly Cys Gly Cys Gly Cys Thr Thr Thr Gly Ala Gly Gly Ala Thr
                 85                  90                  95

Cys Cys Ala Ala Cys Ala Cys Gly Gly Cys Gly Ala Cys Cys Cys Thr
            100                 105                 110

Ala Cys Ala Ala Gly Cys Thr Ala Cys Cys Thr Gly Ala Thr Cys Thr
        115                 120                 125

Gly Thr Gly Cys Ala Cys Gly Gly Ala Ala Cys Thr Gly Ala Ala Cys
    130                 135                 140

Ala Cys Thr Thr Cys Ala Cys Thr Gly Cys Ala Ala Gly Ala Cys Ala
145                 150                 155                 160

Thr Ala Gly Ala Ala Ala Thr Ala Ala Cys Thr Gly Thr Gly Thr
                165                 170                 175

Ala Thr Ala Thr Thr Gly Cys Ala Ala Gly Ala Cys Ala Gly Thr Ala
            180                 185                 190

Thr Thr Gly Gly Ala Ala Cys Thr Thr Ala Cys Ala Gly Ala Gly Gly
        195                 200                 205

Thr Ala Thr Thr Thr Gly Ala Ala Thr Thr Gly Cys Ala Thr Thr
    210                 215                 220

Thr Ala Ala Ala Gly Ala Thr Thr Ala Thr Thr Gly Thr
225                 230                 235                 240

Gly Thr Gly Thr Ala Thr Ala Gly Ala Gly Ala Cys Ala Gly Thr Ala
                245                 250                 255
```

```
Thr Ala Cys Cys Gly Cys Ala Thr Gly Cys Thr Gly Cys Ala Gly Gly
                260                 265                 270
Cys Cys Ala Thr Ala Ala Ala Thr Gly Thr Ala Thr Ala Gly Ala Thr
            275                 280                 285
Thr Thr Thr Thr Ala Thr Thr Cys Thr Ala Gly Ala Ala Thr Thr Ala
290                 295                 300
Gly Ala Gly Ala Ala Thr Thr Ala Ala Gly Ala Cys Ala Thr Thr Ala
305                 310                 315                 320
Thr Thr Cys Ala Gly Ala Cys Thr Cys Thr Gly Thr Gly Thr Ala Thr
                325                 330                 335
Gly Gly Ala Gly Ala Cys Ala Cys Ala Thr Thr Gly Gly Ala Ala Ala
                340                 345                 350
Ala Ala Cys Thr Ala Ala Cys Thr Ala Ala Cys Ala Cys Thr Gly Gly
                355                 360                 365
Gly Thr Thr Ala Thr Ala Cys Ala Ala Thr Thr Ala Thr Ala Thr Ala
            370                 375                 380
Ala Thr Ala Ala Gly Gly Thr Gly Cys Cys Thr Gly Cys Gly Gly Gly
385                 390                 395                 400
Gly Thr Cys Ala Gly Ala Ala Ala Cys Cys Gly Thr Thr Gly Ala Ala
                405                 410                 415
Thr Cys Cys Ala Gly Cys Ala Gly Ala Ala Ala Ala Cys Thr Thr Thr
                420                 425                 430
Ala Gly Ala Cys Ala Cys Cys Thr Thr Ala Ala Thr Gly Ala Ala Ala
            435                 440                 445
Ala Ala Cys Gly Ala Cys Gly Ala Thr Thr Thr Cys Ala Cys Ala Ala
450                 455                 460
Cys Ala Thr Ala Gly Cys Thr Gly Gly Gly Cys Ala Cys Thr Ala Thr
465                 470                 475                 480
Ala Gly Ala Gly Gly Cys Cys Ala Gly Thr Gly Cys Cys Ala Thr Thr
            485                 490                 495
Cys Gly Thr Gly Cys Thr Gly Cys Ala Ala Cys Cys Gly Ala Gly Cys
            500                 505                 510
Ala Cys Gly Ala Cys Ala Gly Gly Ala Ala Ala Gly Ala Cys Thr Cys
            515                 520                 525
Cys Ala Ala Cys Gly Ala Cys Gly Cys Ala Gly Ala Gly Ala Ala Ala
            530                 535                 540
Cys Ala Cys Ala Ala Gly Thr Ala Gly Gly Ala Thr Cys Thr Gly Gly
545                 550                 555                 560
Ala Thr Cys Cys Gly Gly Cys Thr Cys Cys Ala Thr Gly Cys Ala Thr
                565                 570                 575
Gly Gly Ala Cys Cys Thr Ala Ala Gly Gly Cys Ala Ala Cys Ala Thr
            580                 585                 590
Thr Gly Cys Ala Ala Gly Ala Cys Ala Thr Thr Gly Thr Ala Thr Thr
            595                 600                 605
Gly Cys Ala Thr Thr Thr Ala Gly Ala Gly Cys Cys Cys Cys Ala Ala
            610                 615                 620
Ala Ala Thr Gly Ala Ala Ala Thr Thr Cys Cys Gly Gly Thr Thr Gly
625                 630                 635                 640
Ala Cys Cys Thr Thr Cys Thr Ala Gly Gly Thr Cys Ala Cys Gly Gly
                645                 650                 655
Gly Cys Ala Ala Thr Ala Ala Gly Cys Gly Ala Cys Thr Cys Ala
            660                 665                 670
Gly Ala Gly Gly Ala Ala Gly Ala Ala Ala Ala Cys Gly Ala Thr Gly
```

-continued

```
                        675                 680                 685
Ala Ala Ala Thr Ala Gly Ala Thr Gly Gly Ala Gly Thr Thr Ala Ala
            690                 695                 700
Thr Cys Ala Thr Cys Ala Ala Cys Ala Thr Thr Ala Cys Cys Ala
705                 710                 715                 720
Gly Cys Cys Cys Gly Ala Cys Gly Ala Gly Cys Thr Gly Ala Ala Cys
                725                 730                 735
Cys Ala Cys Ala Ala Cys Gly Thr Cys Ala Cys Ala Cys Ala Ala Thr
                740                 745                 750
Gly Thr Thr Gly Thr Gly Thr Ala Thr Gly Thr Gly Thr Thr Gly Thr
            755                 760                 765
Ala Ala Gly Thr Gly Thr Gly Ala Ala Gly Cys Cys Ala Gly Ala Ala
            770                 775                 780
Thr Thr Gly Ala Gly Cys Thr Ala Gly Thr Ala Gly Thr Ala Gly Ala
785                 790                 795                 800
Ala Ala Gly Cys Thr Cys Ala Gly Cys Ala Gly Ala Cys Gly Ala Cys
                805                 810                 815
Cys Thr Cys Cys Gly Ala Gly Cys Ala Thr Cys Cys Ala Cys Gly Cys
                820                 825                 830
Ala Gly Cys Thr Gly Thr Thr Cys Thr Gly Ala Ala Cys Ala Cys
            835                 840                 845
Cys Cys Thr Gly Thr Cys Cys Thr Thr Thr Gly Thr Gly Thr Gly Thr
        850                 855                 860
Cys Cys Gly Thr Gly Gly Thr Gly Thr Gly Cys Ala Thr Cys Cys
865                 870                 875                 880
Ala Gly Cys Ala Gly Thr Ala Ala
            885
```

<210> SEQ ID NO 15
<211> LENGTH: 474
<212> TYPE: DNA
<213> ORGANISM: Artificial Sequence
<220> FEATURE:
<223> OTHER INFORMATION: codon optimized Flt3L

<400> SEQUENCE: 15

```
atgacccagg actgcagctt ccagcacagc cccattagca gcgacttcgc cgtgaagatt      60
cgcgagctga gcgactacct gctgcaggac taccccgtga ccgtggccag caacctgcag     120
gacgaggagc tgtgcggcgg cctgtggcgc ctggtgctgg cccagcggtg gatggagcgc     180
ctgaagaccg tggccggcag caagatgcag ggcctgctgg agcgcgtgaa caccgagatt     240
cacttcgtga ccaagtgcgc cttccagccc ccccccagct gcctgcgctt cgtgcagacc     300
aacattagcc gcctgctgca ggagaccagc gagcagctgg tggccctgaa gcctggatt     360
acccgccaga acttcagccg ctgcctggag ctgcagtgcc agcccgacag cagcaccctg     420
ccccccccct ggagccccg ccccctggag gccaccgccc ccaccgcccc ctag            474
```

<210> SEQ ID NO 16
<211> LENGTH: 474
<212> TYPE: PRT
<213> ORGANISM: Artificial Sequence
<220> FEATURE:
<223> OTHER INFORMATION: Flt3L

<400> SEQUENCE: 16

```
Ala Thr Gly Ala Cys Cys Cys Ala Gly Gly Ala Cys Thr Gly Cys Ala
1               5                   10                  15
```

-continued

Gly Cys Thr Thr Cys Cys Ala Gly Cys Ala Cys Ala Gly Cys Cys Cys
20 25 30

Cys Ala Thr Thr Ala Gly Cys Ala Gly Cys Gly Ala Cys Thr Thr Cys
35 40 45

Gly Cys Cys Gly Thr Gly Ala Ala Gly Ala Thr Thr Cys Gly Cys Gly
50 55 60

Ala Gly Cys Thr Gly Ala Gly Cys Gly Ala Cys Thr Ala Cys Cys Thr
65 70 75 80

Gly Cys Thr Gly Cys Ala Gly Gly Ala Cys Thr Ala Cys Cys Cys Cys
85 90 95

Gly Thr Gly Ala Cys Cys Gly Thr Gly Gly Cys Cys Ala Gly Cys Ala
100 105 110

Ala Cys Cys Thr Gly Cys Ala Gly Gly Ala Cys Gly Ala Gly Gly Ala
115 120 125

Gly Cys Thr Gly Thr Gly Cys Gly Gly Cys Gly Gly Cys Cys Thr Gly
130 135 140

Thr Gly Gly Cys Gly Cys Cys Thr Gly Gly Thr Gly Cys Thr Gly Gly
145 150 155 160

Cys Cys Cys Ala Gly Cys Gly Gly Thr Gly Gly Ala Thr Gly Gly Ala
165 170 175

Gly Cys Gly Cys Cys Thr Gly Ala Ala Gly Ala Cys Cys Gly Thr Gly
180 185 190

Gly Cys Cys Gly Gly Cys Ala Gly Cys Ala Ala Gly Ala Thr Gly Cys
195 200 205

Ala Gly Gly Gly Cys Cys Thr Gly Cys Thr Gly Gly Ala Gly Cys Gly
210 215 220

Cys Gly Thr Gly Ala Ala Cys Ala Cys Cys Gly Ala Gly Ala Thr Thr
225 230 235 240

Cys Ala Cys Thr Thr Cys Gly Thr Gly Ala Cys Cys Ala Ala Gly Thr
245 250 255

Gly Cys Gly Cys Cys Thr Thr Cys Cys Ala Gly Cys Cys Cys Cys Cys
260 265 270

Cys Cys Cys Cys Ala Gly Cys Thr Gly Cys Cys Thr Gly Cys Gly Cys
275 280 285

Thr Thr Cys Gly Thr Gly Cys Ala Gly Ala Cys Cys Ala Ala Cys Ala
290 295 300

Thr Thr Ala Gly Cys Cys Gly Cys Cys Thr Gly Cys Thr Gly Cys Ala
305 310 315 320

Gly Gly Ala Gly Ala Cys Cys Ala Gly Cys Gly Ala Gly Cys Ala Gly
325 330 335

Cys Thr Gly Gly Thr Gly Gly Cys Cys Cys Thr Gly Ala Ala Gly Cys
340 345 350

Cys Cys Thr Gly Gly Ala Thr Thr Ala Cys Cys Cys Gly Cys Cys Ala
355 360 365

Gly Ala Ala Cys Thr Thr Cys Ala Gly Cys Cys Gly Cys Thr Gly Cys
370 375 380

Cys Thr Gly Gly Ala Gly Cys Thr Gly Cys Ala Gly Thr Gly Cys Cys
385 390 395 400

Ala Gly Cys Cys Cys Gly Ala Cys Ala Gly Cys Ala Gly Cys Ala Cys
405 410 415

Cys Cys Thr Gly Cys Cys Cys Cys Cys Cys Cys Cys Cys Thr Gly Gly
420 425 430

Ala Gly Cys Cys Cys Cys Cys Gly Cys Cys Cys Cys Cys Thr Gly Gly
435 440 445

```
Ala Gly Gly Cys Cys Ala Cys Cys Gly Cys Cys Cys Cys Ala Cys
    450                 455                 460
Cys Gly Cys Cys Cys Cys Cys Thr Ala Gly
465                 470

<210> SEQ ID NO 17
<211> LENGTH: 732
<212> TYPE: DNA
<213> ORGANISM: Artificial Sequence
<220> FEATURE:
<223> OTHER INFORMATION: codon optimized CD40L

<400> SEQUENCE: 17
atggacgcca tgaagcgcgg cctgtgctgc gtgctgctgc tgtgcggcgc cgtgttcgtg      60
agccccagcc gggcgaatga tgcgcaagcg ccgaaatcca aatcgaggac gagcgcaac     120 ctgcacgagg acttcgtgtt tatgaagacc atccaacgct gtaataccgg cgagcgcagc    180
ctgagcctgc tcaattgcga agaaatcaag tcccaattcg agggttcgt caaagacatc     240 atgctgaata aggaagaaac caagaaggag aactccttcg agatgcagaa gggcgaccaa    300
aaccccagaa tcgccgccca cgtgatcagc gaagcgtcca gcaagaccac cagcgtcctg    360
caatgggccg agaagggcta ttatacgatg tccataatc tggtgacgct cgagaacggc     420
aagcaactca cggtgaagcg ccagggcctg tactacattt acgcgcaggt gacgttttgc    480
agcaaccgcg aggccagcag ccaggccccc ttcatcgcgt ccctgtgtct gaaaagcccg    540
ggccgctttg aacgcattct gctgcgcgcc gccaacacgc atagcagcgc gaagccctgc    600
ggccagcaga gcatccatct gggcggcgtg ttcgagctgc agcccggcgc cagcgtcttc    660
gtcaacgtga ccgacccctc ccaggtctcc cacgggaccg ggtttaccag cttcgggctg    720
ctgaagctgt ga                                                        732

<210> SEQ ID NO 18
<211> LENGTH: 732
<212> TYPE: PRT
<213> ORGANISM: Artificial Sequence
<220> FEATURE:
<223> OTHER INFORMATION: CD40L

<400> SEQUENCE: 18

Ala Thr Gly Gly Ala Cys Gly Cys Cys Ala Thr Gly Ala Ala Gly Cys
  1               5                  10                  15

Gly Cys Gly Gly Cys Cys Thr Gly Thr Gly Cys Thr Gly Cys Gly Thr
             20                  25                  30

Gly Cys Thr Gly Cys Thr Gly Cys Thr Gly Thr Gly Cys Gly Gly Cys
         35                  40                  45

Gly Cys Cys Gly Thr Gly Thr Thr Cys Gly Thr Gly Ala Gly Cys Cys
     50                  55                  60

Cys Cys Ala Gly Cys Cys Gly Gly Gly Cys Gly Ala Ala Thr Gly Ala
 65                  70                  75                  80

Thr Gly Cys Gly Cys Ala Ala Gly Cys Gly Cys Cys Gly Ala Ala Ala
                 85                  90                  95

Thr Cys Cys Ala Ala Ala Thr Cys Gly Ala Gly Gly Ala Cys Gly
                100                 105                 110

Ala Gly Cys Gly Cys Ala Ala Cys Cys Thr Gly Cys Ala Cys Gly Ala
            115                 120                 125

Gly Gly Ala Cys Thr Thr Cys Gly Thr Gly Thr Thr Ala Thr Gly
        130                 135                 140
```

-continued

```
Ala Ala Gly Ala Cys Cys Ala Thr Cys Cys Ala Ala Cys Gly Cys Thr
145                 150                 155                 160

Gly Thr Ala Ala Thr Ala Cys Cys Gly Gly Cys Gly Ala Gly Cys Gly
                165                 170                 175

Cys Ala Gly Cys Cys Thr Gly Ala Gly Cys Cys Thr Gly Cys Thr Cys
            180                 185                 190

Ala Ala Thr Thr Gly Cys Gly Ala Ala Gly Ala Ala Ala Thr Cys Ala
        195                 200                 205

Ala Gly Thr Cys Cys Cys Ala Ala Thr Thr Cys Gly Ala Gly Gly Gly
    210                 215                 220

Gly Thr Thr Cys Gly Thr Cys Ala Ala Ala Gly Ala Cys Ala Thr Cys
225                 230                 235                 240

Ala Thr Gly Cys Thr Gly Ala Ala Thr Ala Ala Gly Gly Ala Ala Gly
                245                 250                 255

Ala Ala Ala Cys Cys Ala Ala Gly Ala Ala Gly Gly Ala Gly Ala Ala
            260                 265                 270

Cys Thr Cys Cys Thr Thr Cys Gly Ala Gly Ala Thr Gly Cys Ala Gly
        275                 280                 285

Ala Ala Gly Gly Gly Cys Gly Ala Cys Cys Ala Ala Ala Ala Cys Cys
    290                 295                 300

Cys Cys Cys Ala Gly Ala Thr Cys Gly Cys Cys Gly Cys Cys Cys Ala
305                 310                 315                 320

Cys Gly Thr Gly Ala Thr Cys Ala Gly Cys Gly Ala Ala Gly Cys Gly
                325                 330                 335

Thr Cys Cys Ala Gly Cys Ala Ala Gly Ala Cys Cys Ala Cys Cys Ala
            340                 345                 350

Gly Cys Gly Thr Cys Cys Thr Gly Cys Ala Ala Thr Gly Gly Gly Cys
        355                 360                 365

Cys Gly Ala Gly Ala Ala Gly Gly Gly Cys Thr Ala Thr Thr Ala Thr
    370                 375                 380

Ala Cys Gly Ala Thr Gly Thr Cys Cys Ala Ala Thr Ala Ala Thr Cys
385                 390                 395                 400

Thr Gly Gly Thr Gly Ala Cys Gly Cys Thr Cys Gly Ala Gly Ala Ala
                405                 410                 415

Cys Gly Gly Cys Ala Ala Gly Cys Ala Ala Cys Thr Cys Ala Cys Gly
            420                 425                 430

Gly Thr Gly Ala Ala Gly Cys Gly Cys Cys Ala Gly Gly Gly Cys Cys
        435                 440                 445

Thr Gly Thr Ala Cys Thr Ala Cys Ala Thr Thr Thr Ala Cys Gly Cys
    450                 455                 460

Gly Cys Ala Gly Gly Thr Gly Ala Cys Gly Thr Thr Thr Thr Gly Cys
465                 470                 475                 480

Ala Gly Cys Ala Ala Cys Cys Gly Cys Gly Ala Gly Gly Cys Cys Ala
                485                 490                 495

Gly Cys Ala Gly Cys Cys Ala Gly Gly Cys Cys Cys Cys Cys Thr Thr
            500                 505                 510

Cys Ala Thr Cys Gly Cys Gly Thr Cys Cys Cys Thr Gly Thr Gly Thr
        515                 520                 525

Cys Thr Gly Ala Ala Ala Ala Gly Cys Cys Cys Gly Gly Gly Cys Cys
    530                 535                 540

Gly Cys Thr Thr Thr Gly Ala Ala Cys Gly Cys Ala Thr Thr Cys Thr
545                 550                 555                 560

Gly Cys Thr Gly Cys Gly Cys Gly Cys Cys Gly Cys Cys Ala Ala Cys
                565                 570                 575
```

```
Ala Cys Gly Cys Ala Thr Ala Gly Cys Ala Gly Cys Gly Ala
            580                 585                 590
Ala Gly Cys Cys Cys Thr Gly Cys Gly Gly Cys Cys Ala Gly Cys Ala
            595                 600                 605
Gly Ala Gly Cys Ala Thr Cys Cys Ala Thr Cys Thr Gly Gly Gly Cys
        610                 615                 620
Gly Gly Cys Gly Thr Gly Thr Thr Cys Gly Ala Gly Cys Thr Gly Cys
625                 630                 635                 640
Ala Gly Cys Cys Gly Gly Cys Gly Cys Cys Ala Gly Cys Gly Thr
            645                 650                 655
Cys Thr Thr Cys Gly Thr Cys Ala Ala Cys Gly Thr Gly Ala Cys Cys
            660                 665                 670
Gly Ala Cys Cys Cys Thr Cys Cys Cys Ala Gly Gly Thr Cys Thr
        675                 680                 685
Cys Cys Cys Ala Cys Gly Gly Gly Ala Cys Cys Gly Gly Gly Thr Thr
        690                 695                 700
Thr Ala Cys Cys Ala Gly Cys Thr Thr Cys Gly Gly Gly Cys Thr Gly
705                 710                 715                 720
Cys Thr Gly Ala Ala Gly Cys Thr Gly Thr Gly Ala
            725                 730
```